United States Patent

Hamers et al.

(10) Patent No.: US 8,093,177 B2
(45) Date of Patent: Jan. 10, 2012

(54) METAL OXIDES HAVING MOLECULAR AND/OR BIOMOLECULAR FUNCTIONALIZATION

(75) Inventors: Robert J. Hamers, Madison, WI (US); Bo Li, Madison, WI (US); Elizabeth C. Landis, Madison, WI (US); Ryan A. Franking, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 374 days.

(21) Appl. No.: 12/266,130

(22) Filed: Nov. 6, 2008

(65) Prior Publication Data

US 2010/0108490 A1    May 6, 2010

(51) Int. Cl.
*B01J 23/00* (2006.01)
*H01L 35/00* (2006.01)
(52) U.S. Cl. ........................................ 502/300; 136/206
(58) Field of Classification Search ............. 204/157.15, 204/157.68; 977/847; 148/272; 502/300, 502/403; 435/287.4; 526/241; 136/204
See application file for complete search history.

(56) References Cited

U.S. PATENT DOCUMENTS

| | | | | |
|---|---|---|---|---|
| 5,858,534 | A * | 1/1999 | Sucholeiki | 428/407 |
| 6,335,201 | B1 * | 1/2002 | Allbritton et al. | 204/400 |
| 6,569,979 | B1 | 5/2003 | Strother et al. | |
| 6,607,994 | B2 * | 8/2003 | Soane et al. | 428/407 |
| 7,390,649 | B2 * | 6/2008 | Klapproth et al. | 435/287.1 |
| 7,563,457 | B2 * | 7/2009 | Cha et al. | 428/402 |
| 7,582,422 | B2 | 9/2009 | Strother et al. | |
| 2002/0137195 | A1 | 9/2002 | Hamers et al. | |
| 2005/0147758 | A1 * | 7/2005 | Mao et al. | 427/372.2 |
| 2005/0266181 | A1 * | 12/2005 | Bi et al. | 428/32.34 |
| 2006/0194008 | A1 * | 8/2006 | Schwartz et al. | 428/34.4 |
| 2008/0110494 | A1 * | 5/2008 | Reddy | 427/74 |
| 2008/0251772 | A1 * | 10/2008 | Rohlfing et al. | 252/586 |
| 2010/0028559 | A1 * | 2/2010 | Yan et al. | 427/558 |
| 2010/0075042 | A1 * | 3/2010 | Friour et al. | 427/256 |
| 2010/0278892 | A1 * | 11/2010 | Krauland et al. | 424/422 |

OTHER PUBLICATIONS

Rajh et al, "Surface Modification of Small Particle TiO2 Colloids with Cysteine for Enhanced Photochemical Reduction: An EPR Study," J. Phys. Chem 1996, v. 100, pp. 4538-4545.*
Kalyanasundaram et al, "Applications of functionalized transition metal complexes in photonic and optoelectronic devices," Coordination Chemistry Reviews v. 77 (1998), pp. 347-414.*
Gratzel, M.,"Photovoltaic performance and long-term stability of dye-sensitized meosocopic solar cells", C.R. Chimie 9, 578-583, 2006.
Galoppini, E., "Linkers for anchoring sensitizers to semiconductor nanoparticles", Coordination Chemistry Reviews 248, 1283-1297, 2004.

(Continued)

*Primary Examiner* — Keith Hendricks
*Assistant Examiner* — Colleen M Raphael
(74) *Attorney, Agent, or Firm* — Bell & Manning, LLC

(57) ABSTRACT

Disclosed herein are methods for functionalizing metal oxides, including tin dioxide. The methods comprise contacting at least one linker precursor comprising a first functional group to a metal oxide and exposing the linker precursor to UV light. The first functional group covalently binds to the metal oxide via a UV light induced reaction. The linker precursor may be an alkene having a vinyl group or an alkyne having an ethynyl group. Other molecules, such as biomolecules and dye molecules, may be bound to the linker precursors. The functionalized metal oxides may be used alone or as coatings on a substrate and find use in a variety of devices, including biosensors and dye sensitized solar cells.

12 Claims, 7 Drawing Sheets

OTHER PUBLICATIONS

Nichols, B.M, "Photochemical Functionalization of Hydrogen-Terminated Diamond Surfaces: A Structural and Mechanistic Study", J. Phys. Chem B, 109, 20938-20947, 2005.

Strother, T., "Photochemical Functionalization of Diamond Films", Langmuir, 18, 968-971, 2002.

Sun, B., "Covalent Photochemical Functionalization of Amorphous Carbon Thin Films for Integrated Real-Time Biosensing", Langmuir, 22, 9598-9605, 2006.

Kim, H., "Photochemical Functionalization of Gallium Nitride Thin Films with Molecular and Biomolecular layers", Langmuir, 22, 8121-8126, 2006.

Strother, T., "Covalent attachment of oligodeoxyribonucleotides to amine-modified Si (001) surfaces", Nucleic Acids Research, vol. 28, No. 18, 3535-3541, 2000.

Colavita, P.E., "Photochemical Grafting of n-Alkenes onto carbon Surfaces: the Role of Photoelectron Ejection", J. Am. Chem. Soc. 129, 13554-13565, 2007.

Nichols, B.M., "Electrical Bias Dependent Photochemical Functionalization of Diamond Surfaces", J. Phys. Chem. B, 110, 16535-16543, 2006.

Yang, W., "DNA-modified nanocrystalline diamond thin-films as stable, biologically active substrates", Nature Materials, vol. 1, Dec. 2002.

Baker, S.E., "Covalent Functionalization for Biomolecular Recognition on Vertically Aligned Carbon Nanofibers", Chem. Mater. 17, 4971-4978, 2005.

Wang, X., "Direct Photopatterning and SEM Imaging of Molecular Monolayers on Diamond Surfaces: Mechanistic Insights into UV-Initiated Molecular Grafting", Langmuir, 23, 11623-11630, 2007.

International Search Report and Written Opinion received in PCT 200962845, May 26, 2010.

Tami L. Lasseter et al, Covalently modified silicon and diamond surfaces: resistance to nonspecific protein adsorption and optimization for biosensing, J. Am. Chem. Soc., 2004, pp. 10200-10221, vol. 126.

Kwangwook Choi et al, Hydrogermylation of Alkenes and Alkynes on Hydride-Terminated Ge(100) Surfaces, Langmuir, 2000, pp. 7737-7741, vol. 16, No. 20.

Paula E. Colavita et al, Enhancement of Photochemical Grafting of Terminal Alkenes at Surfaces via Molecular Mediators, J. Phys. Chem., 2008, pp. 5102-5112, vol. 112, No. 13.

* cited by examiner

METAL OXIDES HAVING MOLECULAR AND/OR BIOMOLECULAR FUNCTIONALIZATION

GOVERNMENT SUPPORT

This invention was made with United States government support awarded by the following agency: National Science Foundation 0706559. The United States government has certain rights in this invention.

FIELD OF THE INVENTION

The present invention relates to methods for functionalizing metal oxides with organic molecules using UV light. The resulting functionalized metal oxides may be used alone or as coatings on substrates. The functionalized metal oxides are well-suited for use in biosensors and dye sensitized solar cells.

BACKGROUND OF THE INVENTION

The preparation of functionalized substrates is an area of interest for many commercial applications ranging from biosensors to energy conversion devices. Biosensors are designed to determine the presence of biomolecules and are often used in biotechnology industries to perform rapid biochemical analysis. These biosensors are adapted to detect and/or quantify various analytes based on known interactions between the analytes and other biomolecules immobilized on a substrate, such as glass. Organosilane chemistry is a typical method used to attach biomolecules to glass. Unfortunately, these and other methods used to immobilize biomolecules on glass substrates suffer from irreproducibility and instability, resulting in increased manufacturing costs and short shelf life.

Oxide materials, especially $TiO_2$, are often used in energy conversion devices. The bonding of molecules such as dye molecules to the surface of $TiO_2$ provides a way to modify the optical properties and enhance the performance of some energy conversion devices, such as dye-sensitized solar cells. These surface molecular layers play an important role in controlling the electrical properties of $TiO_2$ and other oxide materials. These layers are able to modify the density of mid-gap surface states, alter the charge transfer from dye molecules to $TiO_2$, and control the degree to which redox-active species such as $I^-I_3^-$ can undergo direct recombination processes at the surface. Conventional schemes for functionalizing $TiO_2$ use organic molecules having functional groups such as phosphonic acid, carboxylic acid, ester, acid chloride, carboxylate salt, amide, silane, ether, acetylacetonate, and salicylate. See Galoppini, E., *Coordination Chemistry Reviews*, 248 (2004) 1283-1297. In the case of silanes and ethers, the functionalization involves reaction of these functional groups with surface titanol (Ti—OH) groups and, thus, depends on the amount of surface titanol groups. Previous work using ester linkages has shown that there are multiple bonding sites depending on the pH and degree of hydration of the surface. See Finnie, K. S. et al., *Langmuir* 1998, 14, 2744; and Vittadini, A. et al., *J. Phys. Chem. B* 2005, 109, 20938. A problem with these conventional schemes is that the synthetic methods are complex, costly, and time consuming. In addition, many of the resulting linkages to the metal oxides are weak and unstable.

SUMMARY OF THE INVENTION

The present invention provides methods for functionalizing metal oxides with organic molecules. The methods involve using UV light to covalently bind a variety of linker precursors to the surface of a metal oxide. Other desirable molecules, such as dye molecules and biomolecules, may be coupled to the linker precursors for further functionalization of the metal oxides. The functionalized metal oxides may be used alone or as coatings on a variety of substrates and may be incorporated into a variety of devices such as biosensors and dye sensitized solar cells. Compared to conventional methods and conventional functionalized metal oxides, the present invention is able to provide functionalized metal oxides having higher densities of organic molecules as well as greater thermal and chemical stability. Moreover, the disclosed photochemical methods, which do not require high temperature or ultrahigh vacuum, are simpler and more reproducible than the prior art methods.

The methods comprise contacting at least one linker precursor having a first functional group to the surface of a metal oxide and exposing the linker precursor to UV light. A variety of linker precursors and first functional groups may be used. In some embodiments, the linker precursor comprises a substituted or unsubstituted alkene and the first functional group comprises a carbon-carbon double bond or a vinyl group. In other embodiments, the linker precursor comprises a substituted or unsubstituted alkyne and the first functional group comprises a carbon-carbon triple bond or an ethynyl group. Exemplary alkenes and alkynes are described below.

A UV-induced reaction of the first functional group on the linker precursor with the metal oxide covalently binds the linker precursor to the surface of the metal oxide. The reaction product of the linker precursor and the metal oxide (referred to herein as a "linker molecule") comprises an anchoring group (the atomic or molecular group that becomes covalently bound to the metal oxide). The anchoring group may vary. In some embodiments, the anchoring group comprises a carbon, a CH, or a $CH_2$ group. These anchoring groups are distinguished from conventional anchoring groups provided by conventional schemes for functionalizing metal oxides.

The linker precursors may be bifunctional, comprising a second functional group. The linker molecules (i.e., the covalently bound linker precursors) may also include this second functional group. A variety of second functional groups may be used. In some embodiments, the second functional group is a protected or unprotected amine group or a carboxyl group. Other molecules, including dye molecules and biomolecules, may be coupled to the linker molecules via the second functional group. Exemplary dye molecules and biomolecules are described below. Accordingly, the disclosed methods may comprise other steps, including but not limited to reacting any of these, or other desirable molecules, with the second functional groups.

A variety of metal oxides are compatible with the disclosed methods, including but not limited to doped or undoped $TiO_2$, ZnO, $ZrO_2$, or $SnO_2$. In some embodiments, the metal oxide is $TiO_2$. The structure of the metal oxide may vary. Moreover, in some embodiments, the metal oxide may take the form of a film disposed on the surface of a substrate. A variety of substrates may be used, including, but not limited to glass or plastic.

DETAILED DESCRIPTION

Figure 1:
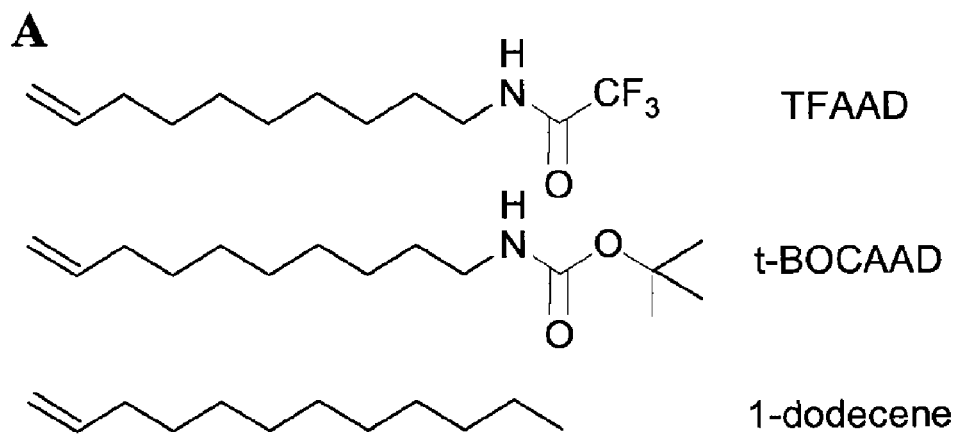
FIG. 1A shows the structures of TFAAD (trifluoroacetamide protected 10-aminodec-1-ene), t-BOCAAD (tert-butyloxycarbamate protected 10-aminodec-1-ene), and 1-dodecene.
FIG. 1B illustrates a method for forming a functionalized metal oxide according to a disclosed embodiment.
Figure 1:
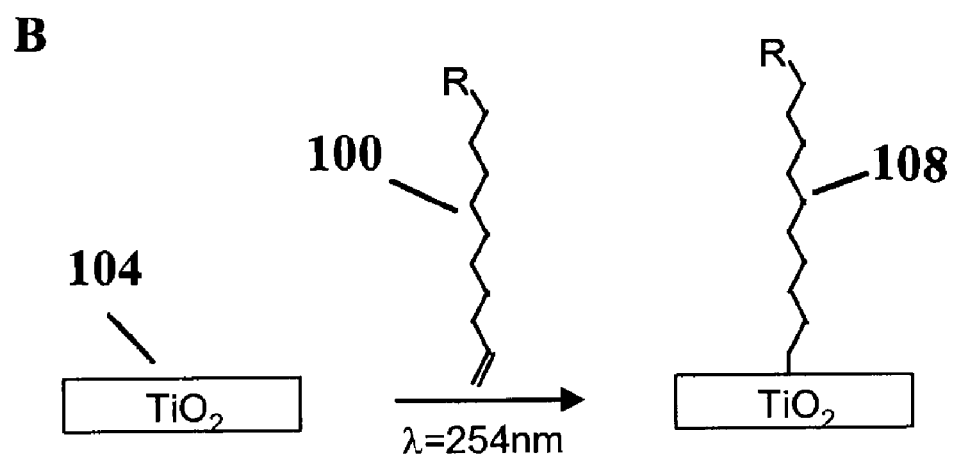

The present invention provides methods for functionalizing metal oxides with organic compounds using UV light. Also disclosed are the functionalized metal oxides, substrates coated with the functionalized metal oxides, and devices incorporating the coated substrates.

The methods comprise contacting at least one linker precursor to the surface of a metal oxide and exposing the linker precursor to UV light. The linker precursors are molecules comprising a first functional group that is capable of covalently binding to the metal oxide via a UV light induced reaction. The particular wavelength of the UV light may vary and may depend upon the identity of the linker precursor and the metal oxide. In some embodiments, the UV light is mid-UV light having a wavelength between 300 nm and 200 nm. In some such embodiments, the UV light is UV light at 254 nm. In other embodiments, the UV light is near-UV light having a wavelength between 400 nm and 300 nm.

The use of light provides a particularly flexible functionalization scheme. Desired portions of the metal oxide may be illuminated to photo-pattern specific linker precursors to specific areas on the metal substrates. Such photo-patterning may provide arrays of linker precursors on the surface of the metal oxide. By way of example only, the metal oxide may be photo-patterned to provide one or more areas having linker precursors covalently bound to the metal oxide and one or more areas without linker precursors. In embodiments having a plurality of areas having covalently bound linker precursors, the linker precursors in one area may be the same or different from the linker precursors in another area.

A variety of linker precursors and first functional groups may be used with the disclosed methods. In some embodiments, the linker precursor comprises a substituted or unsubstituted alkene and the first functional group comprises a carbon-carbon double bond. The phrase "unsubstituted alkene" refers to straight, branched, and cyclic alkenes which do not contain heteroatoms. The number of carbon atoms in the alkene may vary. In some embodiments, the alkene includes 2 to 20 carbon atoms. In other embodiments, the alkene includes 4 to 15 carbon atoms. The phrase "substituted alkene" refers to an unsubstituted alkene as defined above in which one or more bonds to a carbon(s) or hydrogen(s) are replaced by a bond to non-hydrogen and non-carbon atoms. Non-hydrogen and non-carbon atoms include, but are not limited to, a halogen atom such as F, Cl, Br, and I; an oxygen atom in groups such as hydroxyl, alkoxy, aryloxy, carbonyl, carboxyl, and ester groups; a nitrogen atom in groups such as amines, amides, alkylamines, arylamines, and alkylarylamines, and nitriles; and other heteroatoms in various other groups. In other embodiments, the linker precursor comprises a substituted or unsubstituted alkene and the functional group is a vinyl group. By vinyl group, it is meant a —CH=CH$_2$ group.

Non-limiting examples of suitable substituted and unsubstituted alkenes, including those having a vinyl group, include the following: 10-aminodec-1-ene, 11-undecenoate methyl ester, 1-dodecene, 1-butene, 1-pentene, 1-hexene, 1-heptene, 1-octene, 1-nonene, 1-decene, 3-buten-2-one, 3-methyl-1-butene, 3-buten-1-ol, 4-pentenenitrile, 1,4-hexadiene, 3-methyl-1,4-pentadiene, 3-penten-2-one, 3,3-dimethyl-1-butene, 4-methyl-1-pentene, 2-methyl-1-pentene, 2,3-dimethyl-1-butene, 4-penten-1-ol, 2-methyl-3-buten-1-ol, 4-penten-2-ol, 3-methyl-3-buten-1-ol, 2-methyl-3-buten-2-ol, 1-penten-3-ol, 5-hexenenitrile, 2-methyl-1,5-hexadiene, vinylcyclopentane, 5-hexen-2-one, 3-methyl-1-hexene, 4-methyl-1-hexene, 2-methyl-1-hexene, 5-hexen-1-ol, 1-hexen-3-ol, 4-vinyl-1-cyclohexene, 3-butene-1,2-diol, and 3-chloro-1-butene. Substituted alkenes may be protected with a variety of protecting groups, including, but not limited to trifluoroacetic acid and tert-butyloxycarbamate. By way of example only, substituted alkenes include tert-butyloxycarbamate protected 10-aminodec-1-ene and trifluoroacetic acid protected 10-aminodec-1-ene. Structures of these substituted alkenes as well as unsubstituted 1-dodecene are shown in FIG. 1A.

In other embodiments, the linker precursor comprises a substituted or unsubstituted alkyne and the first functional group comprises a carbon-carbon triple bond. The phrase "unsubstituted alkyne" refers to straight, branched, and cyclic alkynes which do not contain heteroatoms. The number of carbon atoms in the alkyne may vary as for the alkenes described above. The phrase "substituted alkyne" has the same meaning with respect to unsubstituted alkyne groups that substituted alkene has with respect to unsubstituted alkenes. However, substituted alkyne also refers to an alkyne in which one or more carbon atoms are bonded to a substituted or unsubstituted alkane, a substituted or unsubstituted alkene, or a substituted or unsubstituted aryl. The phrase unsubstituted alkane refers to straight, branched, and cyclic alkanes which do not contain heteroatoms. The number of carbon atoms in the alkane may vary as for the alkenes described above. The phrase "substituted alkane" has the same meaning with respect to unsubstituted alkane groups that substituted alkene has with respect to unsubstituted alkenes. The phrase "unsubstituted aryl" refers to aryl groups that are not substituted and includes groups containing condensed rings such as naphthalene. The phrase "substituted aryl" has the same meaning with respect to unsubstituted aryl groups that substituted alkene has with respect to unsubstituted alkenes. In other embodiments, the linker precursor comprises a substituted or unsubstituted alkyne and the functional group is a ethynyl group. By ethynyl group, it is meant a —C≡CH group.

Non-limiting examples of suitable substituted and unsubstituted alkenes, including those having a ethynyl group, include the following: 1-butyne, 1-pentyne, 1-hexyne, 1-heptyne, 1-octyne, 1-nonyne, 1-decyne, 1-dodecyne, 2-ethynylanisole, 3-ethynylanisole, 4-ethynylanisole, 2-ethynylbenzyl alcohol, 1-ethynyl-3,5-bis(trifluoromethyl)benzene, 1-ethynylcyclohexene, 1-ethynylcyclopentanol, 2-ethynyl-2,4-difluorobenzene, 1-ethynyl-3,5-difluorobenzene, 1-ethynyl-2-fluorobenzene, 1-ethynyl-3-fluorobenzene, 1-ethynyl-4-fluorobenzene, 1-ethynylnaphthalene, 9-ethynylphenanthrene, 2-ethynylpyridine, 3-ethynylpyridine, 2-ethynyltoluene, 2-ethynyl-trifluorotoluene, 1-ethynyl-2,4,5-trimethylbenzene. Substituted alkynes may be protected with a variety of protecting groups as described above.

The UV-induced reaction of the first functional group on the linker precursor with the metal oxide covalently binds the linker precursor to the surface of the metal oxide. As used herein, the phrase "linker molecule" refers to the reaction product of the linker precursor and the metal oxide. These linker molecules comprise an anchoring group. The phrase "anchoring group," refers to the atomic or molecular group that becomes covalently bound to the metal oxide via the UV light induced reaction described above. The anchoring group will vary, depending upon the identity of the first functional group on the linker precursor. The anchoring group may comprise a carbon, a CH group, or a $CH_2$ group. By way of example only, if the first functional group is a vinyl group, the anchoring group may comprise a $CH_2$ group. However, if the first functional group is a non-terminal carbon-carbon double bond, the anchoring group may comprise a carbon. This carbon may be bonded to a single hydrogen, another carbon, a heteroatom atom, or combinations thereof. By way of another example, if the first functional group is a ethynyl group, the anchoring group may comprise a CH group. However, if the first functional group is a non-terminal carbon-carbon triple bond, the anchoring group may comprise a carbon. This carbon atom may be bonded to another carbon or a heteroatom. Depending upon the type of molecule used for the linker precursor, the linker molecules themselves may comprise a substituted or unsubstituted alkane, a substituted or unsubstituted alkene, or a substituted or unsubstituted alkyne.

The disclosed anchoring groups are distinguished from the conventional anchoring groups provided by conventional schemes for functionalizing metal oxides. As discussed above, in conventional schemes, conventional linker precursors comprising any of the following groups may be reacted with metal oxide surfaces: phosphonic acid, carboxylic acid, ester, acid chloride, carboxylate salt, amide, silane, ether, acetylacetonate, and salicylate. Thus, the resulting conventional anchoring groups will include phosphonic acid or a derivative thereof, carboxylic acid or a derivative thereof, ester or a derivative thereof, acid chloride or a derivative thereof, carboxylate salt or a derivative thereof, amide or a derivative thereof, silane or a derivative thereof, ether or a derivative thereof, acetylacetonate or a derivative thereof, and salicylate or a derivative thereof. The phrase "derivative thereof" refers to the molecular group that is directly bound (either covalently or noncovalently) to the metal oxide after reacting any of disclosed conventional linker precursors with a metal oxide. Thus, in all embodiments of the disclosed methods, the first functional group of the linker precursor is not a phosphonic acid, carboxylic acid, ester, acid chloride, carboxylate salt, amide, silane, ether, acetylacetonate, or salicylate. Similarly, in some embodiments, the anchoring group of the linker molecule is not a phosphonic acid, carboxylic acid, ester, acid chloride, carboxylate salt, amide, silane, ether, acetylacetonate, salicylate or a derivative of any of these groups.

An embodiment of the disclosed method is illustrated in FIG. 1B. As shown in the figure, a substituted alkene 100 having a vinyl group is exposed to a metal oxide 104. The substituted alkene is exposed to UV light at 254 nm. The UV light induces a reaction between the metal oxide and the vinyl group on the substituted alkene 100, thereby providing a covalently bound linker molecule 108 on the surface of the metal oxide 104.

In some embodiments of the disclosed methods, the linker precursor is bifunctional and comprises a second functional group. As described above, covalently bound linker precursors are referred to as linker molecules. Thus, the linker molecules themselves may include this second functional group. The second functional group may be used to couple a variety of desirable molecules to the linker precursor or the linker molecule, as further discussed below. Such molecules may be coupled to the linker precursor before it is covalently bound to the metal oxide or after the linker precursor is covalently bound to the metal oxide (i.e., to the linker molecule). A variety of second functional groups may be used, including, but not limited to an amine group and a carboxyl group. The second functional groups may be protected or unprotected with any of the protecting groups described above.

A variety of metal oxides may be used with the disclosed methods. In some embodiments, the metal oxide comprises $TiO_2$, ZnO, $ZrO_2$, or $SnO_2$. Any of these metal oxides may be doped with other atoms or compounds. By way of example only, the metal oxide may comprise fluorine-doped $SnO_2$ (FTO). In other examples, the metal oxide may comprise indium tin oxide (ITO), a mixture of $In_2O_3$ and $SnO_2$, or antimony tin oxide (ATO), a mixture of $Sb_2O_3$ and $SnO_2$. The metal oxide $TiO_2$ provides a particularly useful metal oxide due to its low fluorescence quenching. $TiO_2$ may be used in a variety of crystal forms, including rutile and anatase.

The characteristics of the metal oxide may vary. In some embodiments, the metal oxide provides a non-porous structure. In some such embodiments, the metal oxide is single-crystalline. In other such embodiments, the metal oxide is polycrystalline. In still other embodiments, the metal oxide provides a nanocrystalline porous structure. The nanocrystalline porous structures provide a greater surface area for attaching linker precursors as compared to non-porous structures having similar dimensions and thicknesses.

The metal oxide may take the form of a film disposed on the surface of a substrate. In such embodiments, the functionalized metal oxide provides a coating for the substrate. A variety of substrates may be used. In some embodiments, the substrate is transparent. In other embodiments, the substrate is glass or plastic. A variety of plastics may be used, including, but not limited to polycarbonates and polyacrylics. The thickness of the metal oxide film may vary.

The disclosed methods may further comprise additional steps. In some embodiments, the linker precursor or linker molecule includes any of the second functional groups disclosed above and the methods further include reacting a dye molecule or a biomolecule with the second functional group. A variety of dye molecules and biomolecules may be used. By way of example only, dye molecules suitable for use in dye sensitized solar cells may be used. Such dyes are known. Non-limiting examples of biomolecules include DNA molecules, RNA molecules, synthetic oligonucleotides, peptides, polypeptides, proteins, enzymes, antibodies, receptors, polysaccharides, and viruses. Synthetic methods for coupling dye molecules and biomolecules to the disclosed second functional groups are well-known. In addition, Example 3 describes a synthetic method for coupling an oligonucleotide to an amine group.

The disclosed functionalized metal oxides may be used in a variety of devices, either alone or as coatings on a substrate.

In some embodiments, the functionalized metal oxides may be used in dye-sensitized solar cells. A basic dye-sensitized solar cell includes a transparent anode, an electrolyte, and a counter electrode. By way of example only, any of the disclosed functionalized metal oxides comprising a dye molecule may be used as a coating on a transparent substrate. The coated transparent substrate may form the anode in a dye-sensitized solar cell. Appropriate electrolytes and materials for counter electrodes are well-known. In other embodiments, the functionalized metal oxides may be used in biosensors. By way of example only, any of the disclosed functionalized metal oxides comprising a biomolecule may be used as a coating on a substrate. The binding of analyte molecules to the immobilized biomolecules may be detected by appropriate imaging techniques. Example 3, below, describes a metal oxide functionalized with oligonucleotides used as a coating over a glass substrate. The fluorescence from fluorescently-tagged complimentary oligonucleotides is used to detect the hybridization of the complimentary oligonucleotide to the immobilized oligonucleotide. Surface plasmon resonance is another imaging technique may be used to detect the binding of analyte molecules to substrates coated with the appropriate functionalized metal oxide and the appropriate metal films.

The present invention, thus generally described, will be understood more readily by reference to the following examples, which are provided by way of illustration and are not intended to be limiting of the present invention.

EXAMPLES

Example 1

Photochemical Grafting of Alkenes on Anatase and Rutile $TiO_2$ Surfaces

Sample Preparation. Single crystalline rutile (001) and (110) $TiO_2$ samples were purchased from MTI Corporation and a natural single crystalline anatase sample was obtained from Hardangervidda, Norway; natural crystals are typically acute dipyramids with large (101) faces and smaller (001) faces exposed. Epitaxial single crystalline anatase (001) films were grown by oxide-assisted molecular beam epitaxy on $SrTiO_3$ substrate at Pacific Northwest National Laboratories. Nanocrystalline anatase samples were prepared using a previously published method similar to that of Gnanasekar et. al., *J. Mater. Res.* (2002), 1507. Titanium isopropoxide in 2-propanol was slowly hydrolyzed with the addition of water, then heated to 85° C. for 4 hours before being dried in an oven at 85° C. overnight. Agglomerated particles were dispersed using a Sonics VCX-130 sonicator, and films were formed by drying aqueous suspensions of the particles on planar substrates. Single crystalline rutile samples and synthetic single crystalline anatase sample were cleaned by ultrasonication in acetone and methanol for 5 minutes and then exposed to ultraviolet light from a low-pressure mercury vapor quartz grid lamp ($\lambda$=254nm, 15 mW/cm$^2$) for 15 min to remove any organic contamination. The natural single crystalline anatase sample was soaked in chloroform for 24 hours without sonication, followed by exposure to UV light in air to remove organic contamination.

Photochemical grafting of alkene molecules to $TiO_2$ surfaces was accomplished by placing the $TiO_2$ sample in a nitrogen-purged reaction chamber and adding ~5 μl of neat alkene, which wets the surface with a thin, liquid film. The samples were covered with a UV-transparent fused quartz window and illuminated with a low-pressure mercury vapor quartz grid lamp ($\lambda$=254 nm, 15 mW/cm$^2$) for the time periods mentioned below. After the photochemical reaction, single crystal $TiO_2$ samples (except for natural single crystalline anatase) were ultra-sonicated in chloroform (5 min) and methanol (5 min) to remove any physisorbed reactants and dried with $N_2$ gas before analysis. The natural single crystalline anatase $TiO_2$ sample was rinsed in chloroform (30 min) and methanol (30 min), and nanocrystalline samples were rinsed in alternating portions of chloroform and methanol for 1 hour.

A number of alkenes were photochemically grafted onto the $TiO_2$ samples, including the ω-unsaturated amine, 10-aminodec-1-ene, that had been protected with a trifluoroacetamide functional group. This alkene is referred to as "TFAAD." TFAAD has a vinyl group at one end for linking to the surface and a protected amine group at the other end that can be deprotected after surface attachment, yielding primary amine groups that can then be used for further functionalization, as further shown in Example 3 below. Other alkenes tested were another ω-unsaturated amine, t-butyloxycarbonyl (t-BOC) protected 10-aminodec-1-ene (referred to as t-BOCAAD), and 1-dodecene. FIG. 1 shows the structures of the three alkenes and illustrates the photochemical grafting of the alkenes on $TiO_2$ surfaces.

Characterization. The crystal structure of the nanocrystalline $TiO_2$ was analyzed using X-ray Diffraction, (Scintag PAD V). The surface monolayers of all $TiO_2$ samples were characterized using X-ray photoelectron spectroscopy (XPS) with a monochromatic Al Kα source (nominal 1486.6 eV photon energy). XPS spectra were recorded with an analyzer resolution of 0.1-0.2 eV, collecting electrons emitted at 45° from the surface normal. Atomic area ratios were determined by fitting raw data to Voigt functions after a baseline correction, and normalizing the peak area ratios by the corresponding atomic sensitivity factors (C=0.296; F=1.000; N=0.477; O=0.711; Ti(2p)=1.798). Infrared reflection-absorption spectra were collected on a Bruker Vector 33 FTIR spectrometer equipped with a VeeMaxII variable angle specular reflectance accessory and a wire grid polarizer. Single crystal spectra were collected using s-polarized light at 30° incidence from the surface normal and nanocrystalline spectra were collected using p-polarized light at 60° incidence from the surface; 500 or 100 scans at 4 cm$^{-1}$ resolution were collected for both background and sample. The spectra were baseline corrected for clarity.

UPS (ultraviolet photoemission spectroscopy) characterization was carried out using a He(I) emission lamp (21.2 eV) as an excitation source and an analyzer resolution of 0.05-0.1 eV. Samples were collected at a takeoff angle of 75° (from the surface plane) and biased -5.00 to -6.50 V with respect to the spectrometer to ensure that the vacuum level of the sample was higher in energy than that of the analyzer. Spectra at progressively higher biases were collected until the high binding energy cutoff was observed to converge; the spectrum obtained at the bias at which convergence was observed was used for the work function calculations. Energies were referenced to the sample Fermi level, which was determined by measurement of Ta clips directly in contact with the sample.

Figure 2:
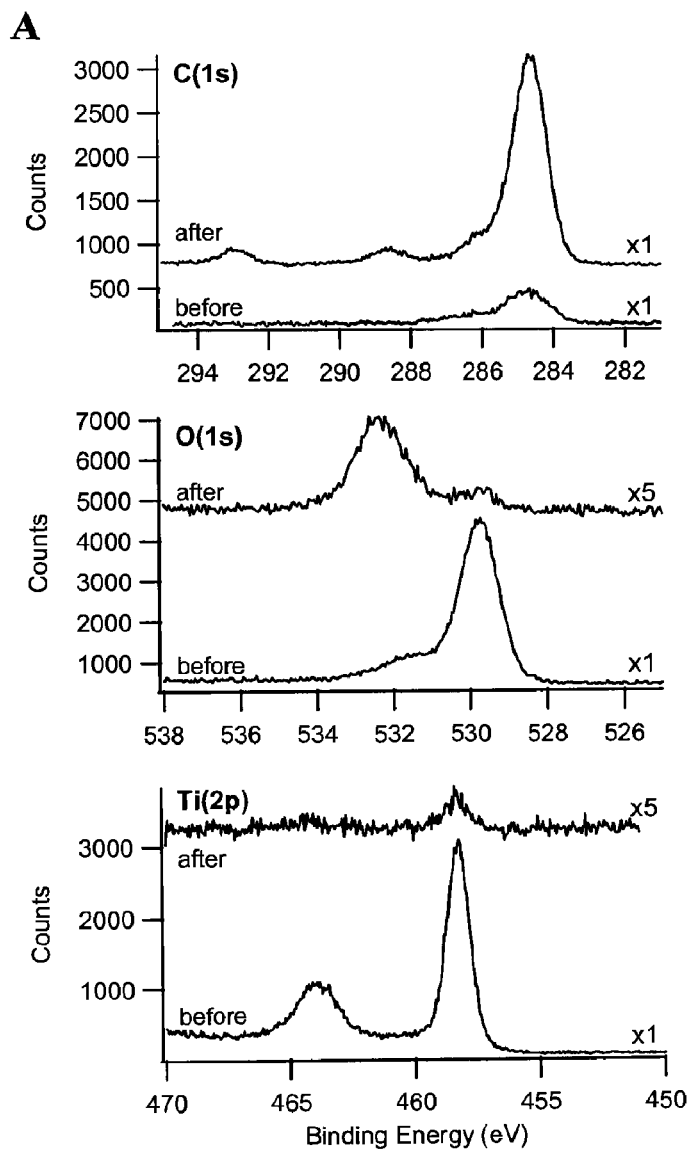
FIG. 2A includes the XPS spectra of a single crystalline rutile (001) TiO$_2$ sample showing the C(1s), O(1s) and Ti(2p) regions. The spectra shown include the sample before and after attachment of TFAAD to a rutile TiO$_2$ surface.
FIG. 2B includes the FTIR spectra of a single crystalline rutile TiO$_2$ (001) sample functionalized with TFAAD.
Figure 2:
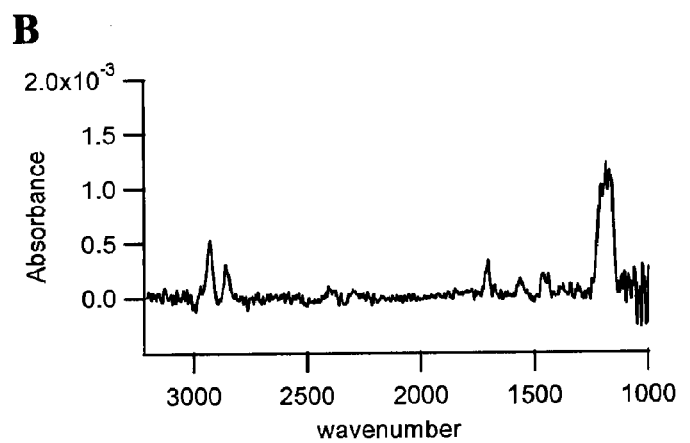

Photochemical Functionalization of Single Crystalline Rutile $TiO_2$ Surfaces with TFAAD. FIG. 2A shows XPS spectra for the C(1s), O(1s) and Ti(2p) areas before and after functionalization of a single crystalline rutile (001) $TiO_2$ surface with TFAAD. The cleaned rutile $TiO_2$ surface shows only a small C(1s) peak at 284.6 eV, demonstrating that carbon contamination levels are low. The O(1s) spectrum shows a strong peak at 529.7 eV and a shoulder at 531.2 eV. The peak at 529.7 eV corresponds to the chemically distinct lattice oxygen and the shoulder at 531.2 eV arises from the absorbate oxygen atoms including carboxyl acid and hydroxyl groups. Since chemical shifts associated with changes in surface chemistry are of primary interest (rather than changes in band-bending), this lattice oxygen 1s peak at 529.7 eV was used as a reference for other peaks. The titanium peaks at 458.4 eV and 464.4 eV are attributed to the $2p_{3/2}$ and $2p_{1/2}$ peaks of lattice titanium, respectively. After the photochemical functionalization step, the C(1s) spectrum shows a strong peak at 284.7 eV, a weak shoulder near 286.1 eV, and two smaller peaks at 288.6 and 293 eV. The peak at 284.7 eV comes from the alkyl chain of TFAAD. The peaks at 288.6 and 293 eV are attributed to the C atoms of the carbonyl (C=O) group and the —$CF_3$ group, respectively, while the small shoulder at 286.1 eV is from the C atom adjacent to the N atom. The O(1s) spectrum shows a peak at 532.3 eV from the oxygen atoms of the trifluoroacetamide functional groups of TFAAD monolayers and a peak at 529.7 eV from the lattice oxygen attenuated by the TFAAD layer. The absolute Ti(2p) signals are also attenuated to approximately 5% of their original values by the grafted TFAAD layer.

The organic films were also characterized using Infrared Reflection Absorption Spectroscopy (IRRAS). FIG. 2B shows the spectrum of a single-crystal rutile (001) $TiO_2$ sample after grafting of TFAAD for 18 hours. The spectrum displays the C=O amide stretching peak at 1701 $cm^{-1}$ and the three C—F stretching peaks of the trifluoroacetamide functional group at 1167, 1182 and 1205 $cm^{-1}$. It also shows the symmetric and asymmetric $CH_2$ stretching peaks of alkyl chain at 2858 and 2924 $cm^{-1}$, respectively.

Taken together, both XPS and FTIR data show successful grafting of TFAAD onto a single crystalline rutile (001) $TiO_2$ surface.

To determine whether the photochemical reaction with TFAAD depends on the crystal orientation of a single crystalline rutile $TiO_2$ samples, a single-crystal rutile (110) $TiO_2$ surface was functionalized with TFAAD for 6.5 hours and characterized using XPS. The XPS spectra (not shown) yielded an area ratio $A_{F(1s)}/A_{Ti(2p)}$, of 5.3, which is higher than the value of 2.1 observed on the single-crystal rutile (001) $TiO_2$ surface functionalized with TFAAD for 7.5 hours. Thus, grafting occurs more readily on the (110) surface. The rutile (110) surface has both 5-fold coordinated and 6-fold coordinated Ti atoms; the six-coordinate Ti atoms are capped with bridging oxygens that link adjacent Ti sites. In contrast, the (001) surface is composed of the 4-fold coordinated Ti cations with two oxygens within the surface plane and the other two in the plane below. Because the bridging oxygens are only weakly bound to the surface, the (001) surface is calculated to be lower in energy than the (110) surface. Regarding the differences in reactivity between the surfaces, it is possible that UV illumination creates some in-plane oxygen vacancies on the (001) face, which in turn assists in the photoemission process.

Photochemical Functionalization of Single Crystalline and Nanocrystalline Anatase $TiO_2$ Surfaces with TFAAD. The anatase form of titanium dioxide is of interest because while less stable than rutile, this crystal structure shows increased performance for photovoltaic energy conversion and photocatalysis. To compare the reaction efficiency of anatase $TiO_2$ samples with rutile ones, TFAAD molecules were grafted onto synthetic single crystal anatase (001) $TiO_2$ thin films grown on $SrTiO_3$ substrates, a natural single anatase (101) crystal, and nanocrystalline $TiO_2$ films prepared by dispersing anatase nanocrystals onto a substrate consisting of a glass surface with a thin coating of fluorinated tin oxide.

Figure 3:
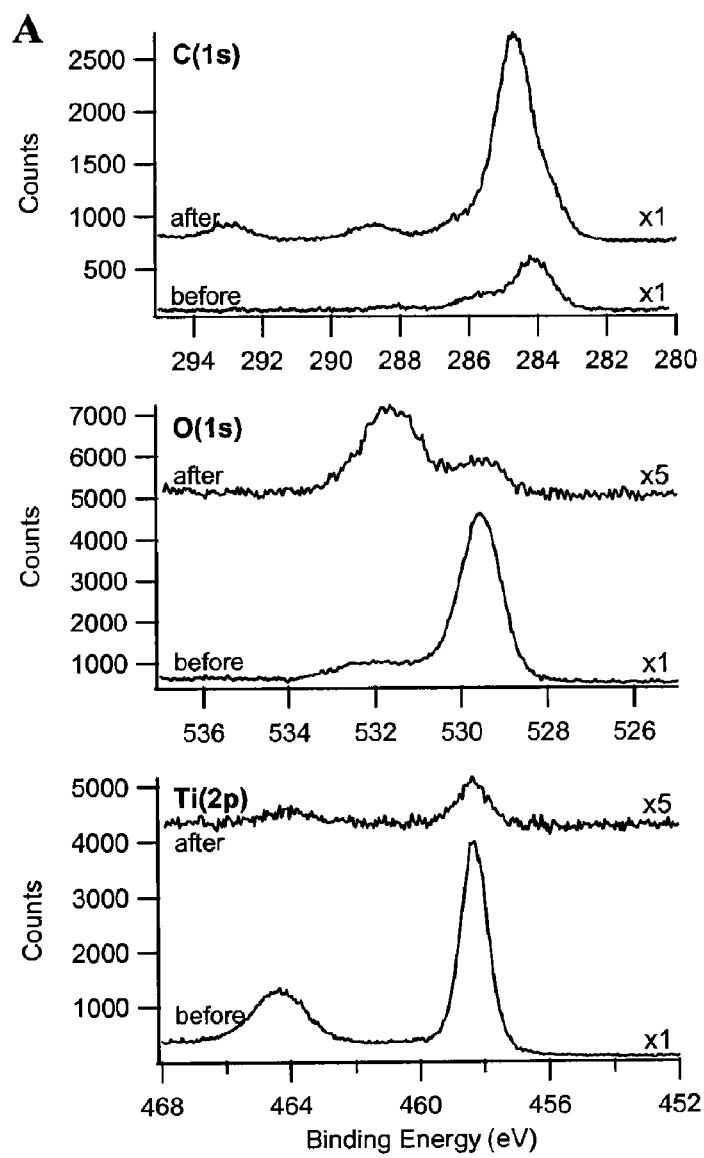
FIG. 3A includes the XPS spectra of a single crystalline anatase (001) TiO$_2$ sample showing the C(1s), O(1s) and Ti(2p) regions. The spectra shown include the sample before and after attachment of TFAAD to an anatase TiO$_2$ surface.
FIG. 3B includes the O(1s) spectrum of nanocrystalline anatase TiO$_2$ samples functionalized with TFAAD at three different illumination times.
Figure 3:
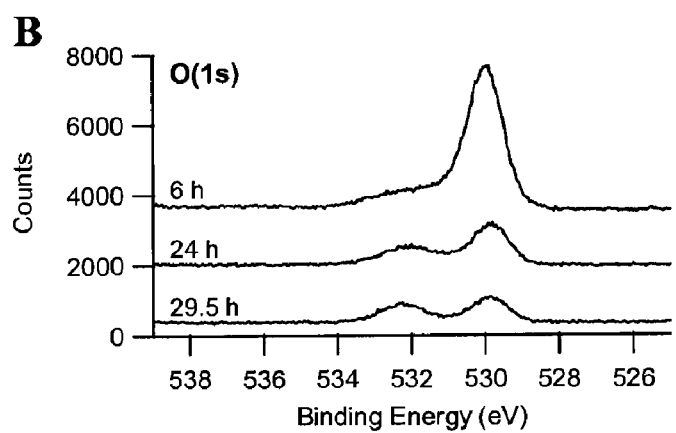

FIG. 3A shows the C(1s), O(1s) and Ti(2p) XPS spectra for the synthetic single-crystal anatase (001) $TiO_2$ thin film before and after photochemical grafting of TFAAD (data shown after 39 hours). XPS spectra (not shown) obtained on the natural single-crystal anatase (101) sample was qualitatively similar to the spectra obtained on rutile $TiO_2$. However, a comparison of the XPS peak areas shows that the extent of reaction is significantly different on (001) and (101) crystal faces. The $A_{F(1s)}/A_{Ti(2p)}$ ratio after a grafting time of 7 hours is 4.6 on the anatase (101) sample, but only $A_{F(1s)}/A_{Ti(2p)}$ of 0.94 on the anatase (001) surface. Regarding these differences in reactivity, it is known that the most stable anatase (101) surface shows the highest concentration of oxygen-vacancy defects, while the anatase (001) surface typically shows a much lower concentration of oxygen vacancies. See Thomas, A. G.; Flavell, W. R.; Mallick, A. K.; Kumarasinghe, A. R.; Tsoutsou, D.; Khan, N.; Chatwin, C.; Rayner, S.; Smith, G. C.; Stockbauer, R. L.; Warren, S.; Johal, T. K.; Patel, S.; Holland, D.; Taleb, A.; Wiame, F. *Phys. Rev. B* 2007, 75, 035105; Thomas, A.G.; Flavell, W. R.; Kumarasinghe, A. R.; Mallick, A. K.; Tsoutsou, D.; Smith, G. C.; Stockbauer, R. L.; Patel, S.; Gratzel, M.; Hengerer, R. *Phys. Rev. B* 2003, 67, 035110; and Herman, G. S.; Sievers, M. R.; Gao, Y. *Phys. Rev. Lett.* 2000, 84, 3354. This trend matches the photochemical reactivity of TFAAD on anatase (001) and (101) surfaces.

The XPS data and FTIR data (not shown) for the nanocrystalline $TiO_2$ samples were nearly identical to those observed after grafting of TFAAD monolayers onto a single-crystal rutile (001) $TiO_2$. FIG. 3B shows the O(1s) spectrum of nanocrystalline anatase $TiO_2$ samples functionalized with TFAAD at three different illumination times (6, 24 and 29.5 hours). As the illumination time increases, the peak at 529.7 eV from the lattice oxygen decreases because of attenuation by the TFAAD monolayer, while the peak at 532.3 eV from the oxygen atoms of the trifluoroacetamide functional group increased.

Figure 4:
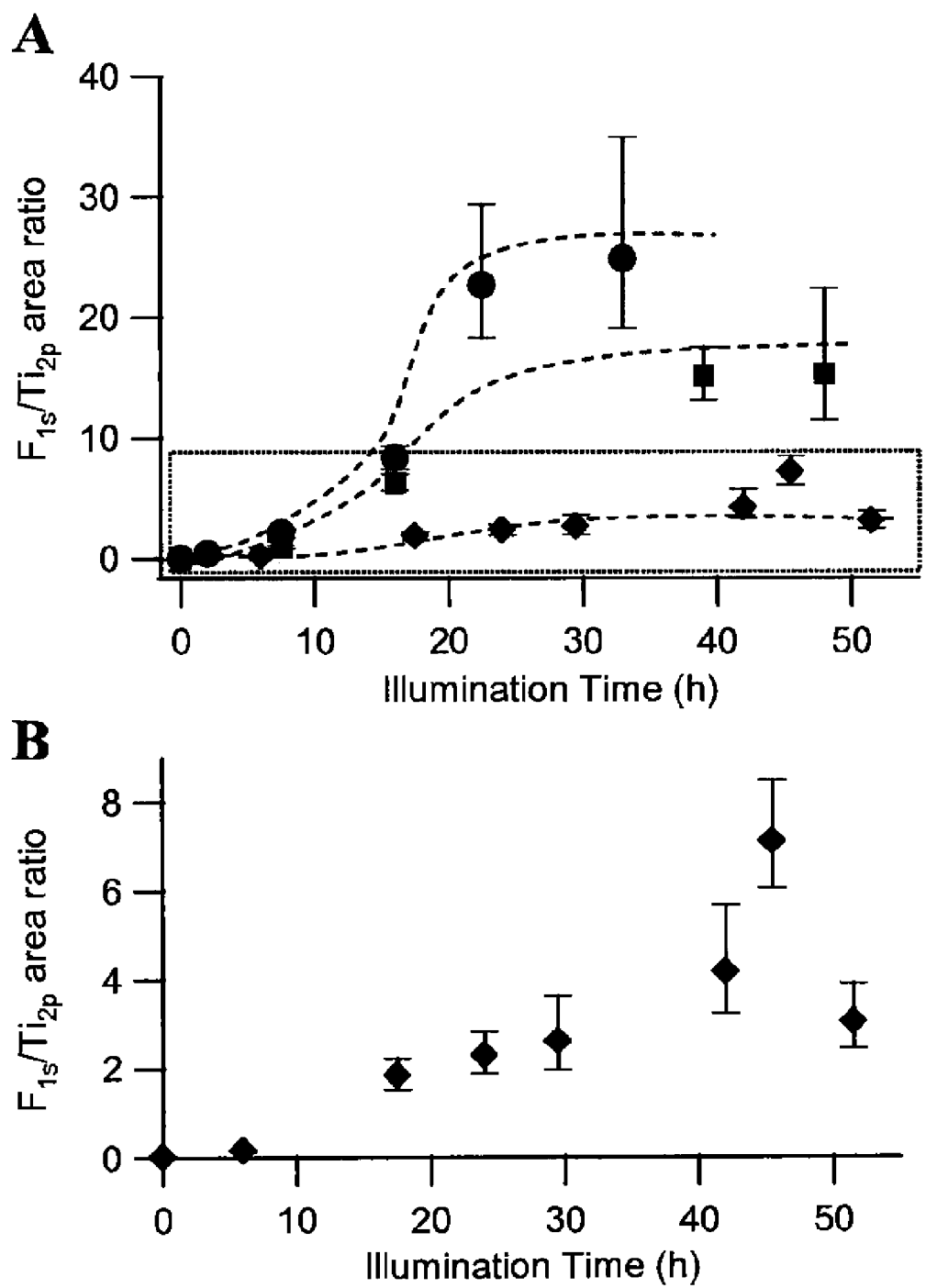
FIG. 4A depicts the functionalization of single crystalline rutile (001), single crystalline anatase (001) and polycrystalline anatase TiO$_2$ surfaces with TFAAD as a function of illumination time.
FIG. 4B shows an enlarged portion of FIG. 4A (the dotted rectangle).

Kinetic Studies of Photochemical Functionalization. To characterize the dependence of functionalization rate on the crystal structure (rutile vs. anatase), the reaction of TFAAD with the rutile (001) and anatase (001) single crystals was monitored, along with a nanocrystalline $TiO_2$ film. The $A_{F(1s)}/A_{Ti(2p)}$ ratio was used as a measure of the extent of surface reaction. As shown in FIG. 4A, the $A_{F(1s)}/A_{Ti(2p)}$ ratio (circles) for the single-crystal rutile (001) $TiO_2$ sample increased slowly at first and then reached a limiting value of 24.8 after 25 hours. The $A_{F(1s)}/A_{Ti(2p)}$ ratio obtained from the anatase (001) sample (squares) saturates at 15.3 after 30 hours. The fact that the limiting peak area ratio is obtained under conditions where XPS intensity from the underlying bulk $TiO_2$ is still clearly observed proves that the photochemical surface functionalization self-terminates. Molecules react with the surface until some maximum coverage is reached, and then reaction with the surface stops. Single crystalline rutile (001) sample reaches this limiting coverage faster than single crystalline anatase (001). The difference in limiting values between these two samples suggests that the maximum density may also be slightly different. Both samples show an induction period at the beginning of the reaction, which may be related to the UV-induced formation of surface defects, such as oxygen vacancies.

FIGS. 4A and 4B show the reaction extent for nanocrystalline $TiO_2$ samples (diamonds) exposed to TFAAD. FIG. 4B is an enlarged version of the region enclosed by the dotted rectangle in FIG. 4A. The $A_{F(1s)}/A_{Ti(2p)}$ ratio obtained from nanocrystalline anatase samples saturates at 3.0 after 35 hours, which is lower than the single crystalline rutile (001) and single crystalline anatase (001) samples. The nanocrystalline sample also shows an induction period for approximately 1 hour at the beginning of the reaction.

Photochemical Functionalization with Other Terminal Alkenes. Rutile (001) and anatase (001) $TiO_2$ samples were prepared and reacted with 1-dodecene, t-BOCAAD and TFAAD using 254 nm illumination for 22 hours. XPS spectra (not shown) indicated that all three molecules clearly graft to the respective surfaces. However, grafting of TFAAD led to a clear decrease in the O(1s) intensity due to scattering. Table 1 shows the $A_{C(1s)}/A_{Ti(2p)}$ ratio of $TiO_2$ (001) samples functionalized with these three molecules after correction with the atomic sensitivity factors.

TABLE 1

C(1s)/Ti(2p) area ratios of single crystalline rutile (001) and anatase (001) $TiO_2$ samples functionalized with 1-dodecene, t-BOCAAD and TFAAD.

|  | cleaned | 1-dodecene | t-BOCAAD | TFAAD |
|---|---|---|---|---|
| Rutile $A_{C(1s)}/A_{Ti(2p)}$ | 0.35 | 2.3 | 7.9 | >50 |
| Anatase $A_{C(1s)}/A_{Ti(2p)}$ | 0.91 | 3.2 | 19 | 29 |

These data show that 1-dodecene has slightly lower reactivity than t-BOCAAD, while TFAAD yields an anomalously high coverage that is consistent with multilayer formation. From a mechanistic standpoint, however, it is important to note that while a simple exciton-mediated reaction with the organic olefin group would predict that all three molecules would have similar reactivity, it is clear from these data that the terminal functional group (i.e., t-BOC and TFA) influences reactivity. Notably, density functional calculations showed that the three alkenes have quite different electron affinities. See Colavita, P. E.; Sun, B.; Tse, K. Y.; Hamers, R. J. *J. Am. Chem. Soc.* 2007, 129, 13554. The data presented here show that reactivity increases as electron affinity increases. TFAAD has the lowest-lying acceptor level (largest electron affinity) and yielded the highest reactivity, t-BOCAAD has a higher-lying acceptor level (smaller electron affinity) and yielded lower reactivity, while 1-dodecene has the highest-lying acceptor level and was the least reactive.

It is notable that even 1-dodecene, which does not contain any oxygen atoms, leads to a pronounced change in the O(1s) spectrum. A more detailed analysis of the O(1s) and Ti(2p) areas shows that grafting of 1-dodecene to the surface decreases the total integrated Ti(2p) and O(1s) intensities by nearly the same ratio. Thus, grafting of 1-dodecene does not significantly change the total amount of oxygen present, but does lead to a pronounced increase in the high-BE peak. This peak has often been attributed to titanol groups on the surface (Ti—OH), but a peak at nearly the same energy should be produced by Ti—O—C linkages, due to the similarity in electronegativity of hydrogen (Pauling electronegativity=2.20) and carbon (electronegativity =2.55).

The experiments described above show that single crystalline rutile and anatase $TiO_2$ and nanocrystalline anatase $TiO_2$ surfaces can be photochemically functionalized with organic alkenes by illumination with ultraviolet (UV) light at 254 nm (photon energy=4.9 eV).

Example 2

Photochemical Grafting of Alkenes on $TiO_2$ Coated Glass Substrates

Fluorinated tin oxide (FTO)-coated glass substrates with a resistivity of 15 ohm/sq were obtained from Hartford Glass Co. and were cleaned by rinsing with acetone and methanol. FTO-coated glass was used because of its electrical conductivity, but identical procedures would be expected to be work with uncoated (bare) glass. The substrates were coated with $TiO_2$ by a two-step procedure. The samples were first immersed in a 50 mM aqueous $TiCl_4$ solution for 30 min at 70° C. to prepare a dense layer of $TiO_2$ on the surface.

To prepare nanocrystalline $TiO_2$ films, a paste containing 20 nm $TiO_2$ anatase particles (Ti-Nanoxide T20/SP, purchased from Solaronix, Inc.) was screen printed onto the glass through a 90 threads/cm polyester mesh and dried at 125° C. for 5 min. The $TiO_2$ was printed and dried two more times for a total of three layers, creating a 7-10 μm thick film. The films were then placed on a hot plate and heated to 325° C. for 5 min, 375° C. for 5 min, 450° C. for 15 min, and finally to 500° C. for 15 mins. before being allowed to cool to room temperature. A final UV-ozone cleaning was usually performed overnight before films were ready for use. This procedure produces glass surfaces coated with a nanocrystalline thin film of $TiO_2$ particles. Such nanocrystalline films are porous and have a high internal surface area.

Non-porous $TiO_2$ films were prepared by coating the glass surfaces with a thin film of titanium (by thermal or electron-beam evaporation) and subsequently oxidizing the Ti to $TiO_2$ in air to produce flat $TiO_2$ surfaces.

To clean the samples, the $TiO_2$ films on glass were exposed to UV light at 300 K for 1 h in air. The UV lamp generates ozone which oxidizes and removes any residual organic contamination.

Photochemical grafting of 1-dodecene was carried out as described in Example 1. Briefly, 5 μL of the alkene was dripped onto the $TiO_2$-coated glass surface, covered with a quartz window, and illuminated using ultraviolet (UV) light (254 nm) from a low-pressure mercury lamp for 8-16 hours while maintaining a flow of nitrogen gas. Covalent attachment of the alkene to the $TiO_2$ film was confirmed by infrared and Raman spectroscopy measurements. To test the thermal stability of the resulting molecular coating, samples were exposed to hot water for varying lengths of time, and the intensity of C—H stretching vibrations were monitored using IR spectroscopy. For the nanocrystalline $TiO_2$ films, no degradation was detectable after more than 600 hours in water at 60° C. or after more than 180 minutes in water at 85° C.

Example 3

Biofunctionalization of Alkenes Grafted Onto $TiO_2$ Coated Glass Substrates

To link DNA to the $TiO_2$-coated glass surfaces, TFAAD was grafted onto the surface using the procedure described in Example 2. The trifluoroacetamide (TFA) protecting group was removed by immersing the sample in a solution of 0.064 M $NaBH_4$ in 10 ml anhydrous methanol at room temperature for 30 minutes, and then at 65° C. for about 8 h. This procedure yielded a surface terminated with molecular monolayers bearing primary amine groups at the surface. To link DNA to the exposed amine groups, the amine-modified surfaces were exposed to a 1 mM solution of the heterobifunctional cross-linker sulfosuccinimidyl 4-(N-maleimidomethyl) cyclohexane-1-carboxylate (SSMCC) in triethanol amine buffer solution (pH 7) for 2 hours. DNA oligonucleotides modified with a thiol group at the 5' end (DNA1) were then linked to this surface by applying 5 μL of 250 μM thio-oligonucleotide and keeping the sample in a humid reaction vessel for at least 6 h. Any remaining DNA was removed by thorough rinsing and soaking twice in HB (hybridization buffer) buffer for 10 min.

The sequence of DNA oligonucleotide used to modify the surface was 5'-HS-GCT TAT CGA GCT TTC G-3' (DNA1). Next, the hybridization of the surface-bound strand was studied using single-stranded DNA oligonucleotides labeled with a fluorescein tag at the 5' end (5'-FAM-CG AAA GCT CGA TAA GC-3' (cDNA1)). cDNA1 is a perfect complementary match to DNA1. All DNA strands were purchased from the Biotechnology Center of the University of Wisconsin-Madison.

The stability of the surface-bound oligonucleotides was evaluated by testing the amount of DNA that would hybridize to an DNA1-modified sample in 25 repeated cycles of hybridization and denaturation. In each cycle, the sample was exposed to the fluorescently labeled complement (cDNA1) for 5 min at room temperature in a humid chamber, rinsed in 2×SSPE buffer (0.2 M sodium phosphate buffer, pH ~7.4, with 0.3 M NaCl and 0.002 M EDTA) twice, 5 min each, and the intensity of fluorescence was measured. The sample was then denatured in an aqueous solution of 8.3 M urea for 4 min at 65° C., rinsed with distilled water, and rehybridized. This hybridization/denaturation process was repeated 25 times. The intensity was occasionally measured after denaturation, to ensure that this step removed all of the hybridized DNA between cycles. For the nanocrystalline $TiO_2$ films, the resulting fluorescence measurements showed no significant loss of DNA even after 25 hybridization cycles. Similar results were obtained on non-porous $TiO_2$ films.

Example 4

Photochemical Grafting of Alkenes on Other Metal Oxide Surfaces

Fluorine doped tin oxide (as a thin film on a glass substrate) and zinc oxide single crystal surfaces were used as purchased. Zinc oxide was purchased from MTI Corporation. Fluorine doped tin oxide coated glass was purchased from Hartford Glass, Inc. Zirconium oxide surfaces were fabricated by evaporating a thin film of zirconium (using electron-beam evaporation) onto a silicon wafer substrate and letter the Zr film oxidize at room temperature in air. Photochemical grafting of TFAAD on the metal oxide surfaces was conducted as described in Example 2. After completion of the reaction, the nonspecifically bound alkene was removed by soaking the surfaces in organic solvents, typically methanol and chloroform.

Figure 5:
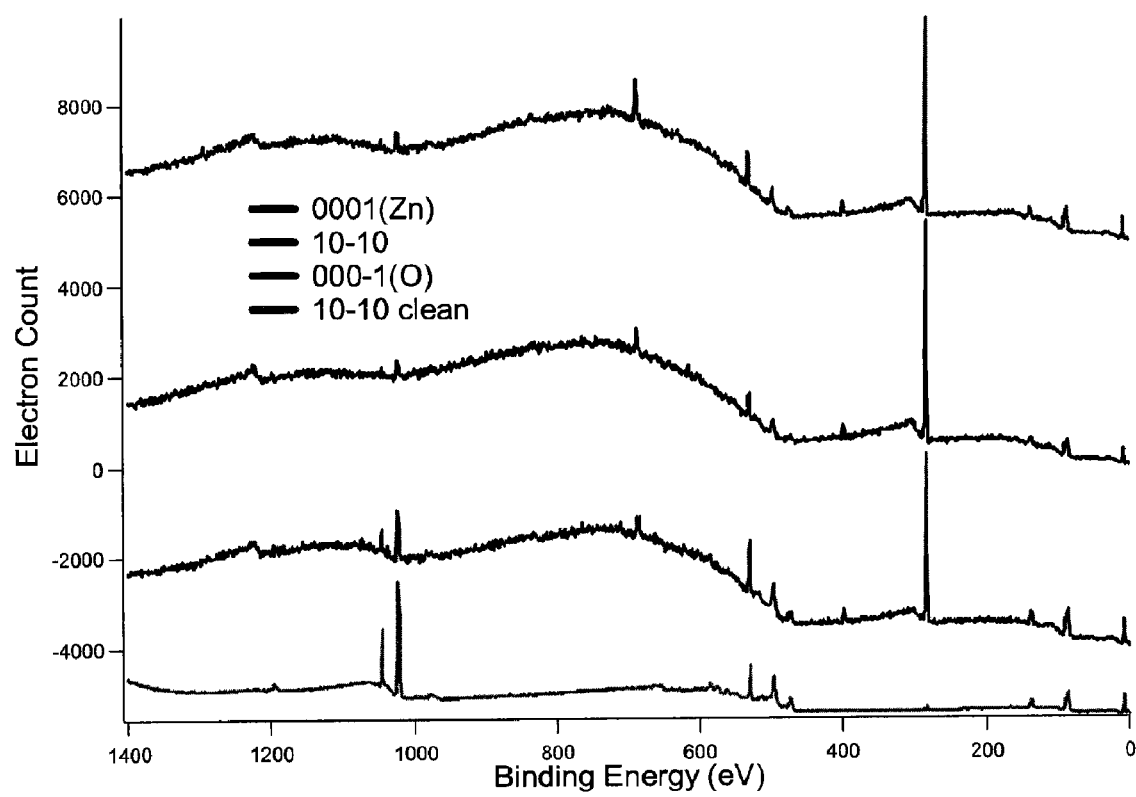
FIG. 5 shows XPS spectra of TFAAD on three different zinc oxide crystal faces and a XPS spectrum of a control sample ("10-10 clean").

FIG. 5 shows XPS spectra of TFAAD on three different zinc oxide crystal faces. The clean sample (i.e., control sample) shows the absence of fluorine and carbon peaks around 700 eV and 300 eV, respectively, while the three functionalized crystal faces show the growth of both fluorine and carbon peaks from covalently bound TFAAD.

Figure 6:
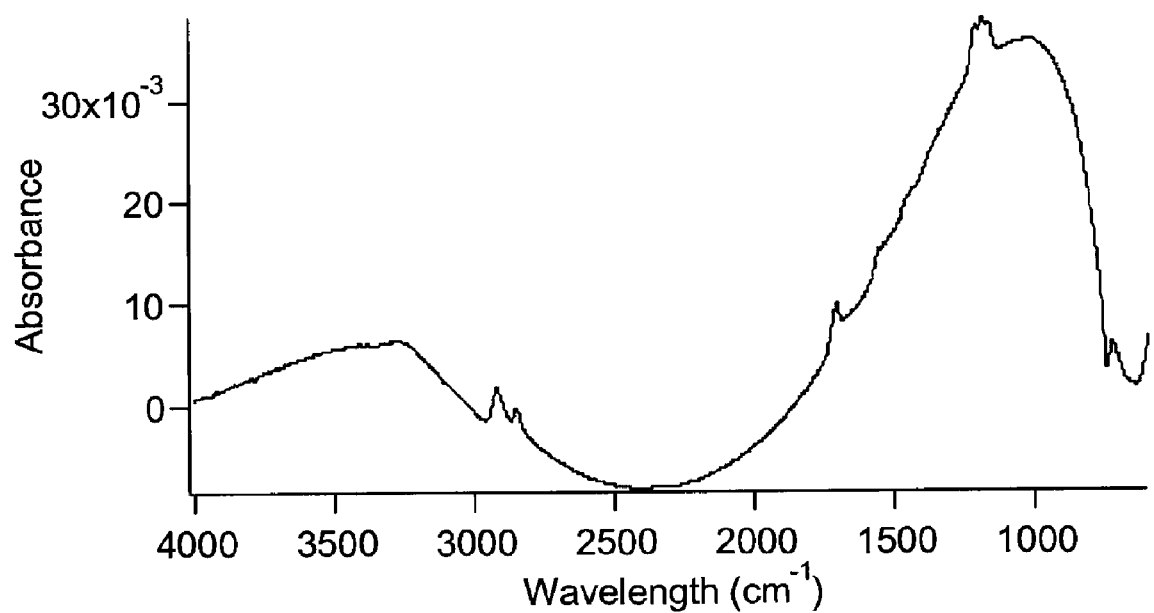
FIG. 6 shows the IR spectrum of TFAAD on fluorine-doped tin oxide.

FIG. 6 shows the IR spectrum of TFAAD on fluorine doped tin oxide. The spectrum includes the expected peaks for TFAAD, including the two peaks at ~2900 $cm^{-1}$ corresponding to $CH_2$ stretching; the peak at 1800 $cm^{-1}$ corresponding to C=O stretches; and the three peaks at ~1200 $cm^{-1}$ corresponding to the three C—F stretches.

Figure 7:
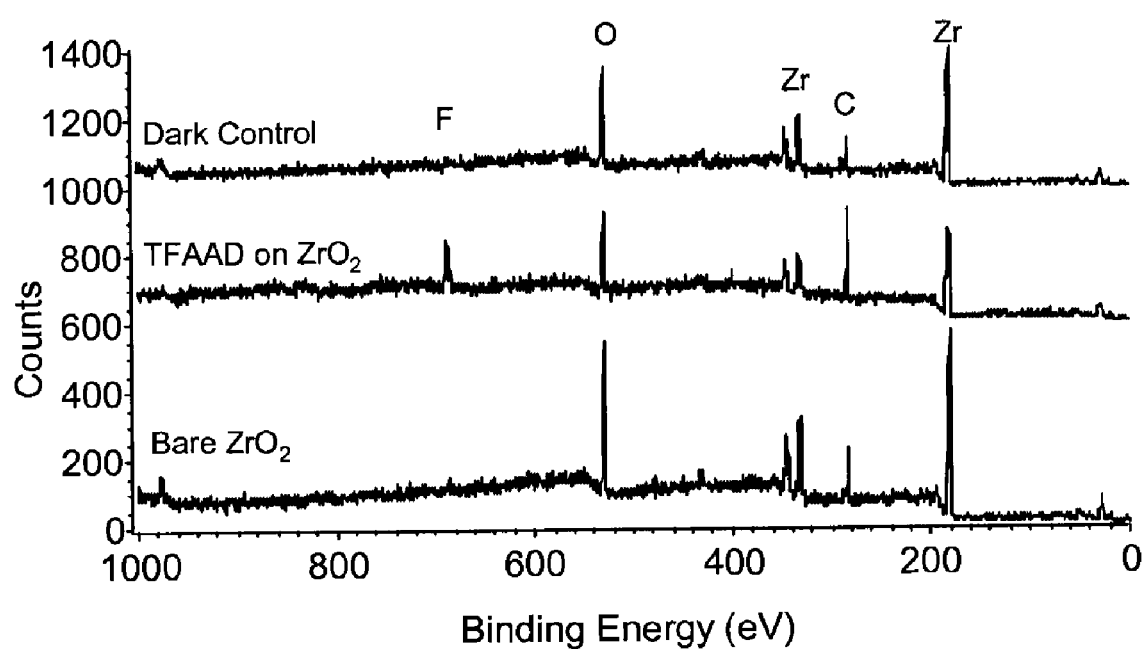
FIG. 7 shows XPS spectra of TFAAD on zirconium oxide, bare zirconium oxide, and a sample exposed to TFAAD but no UV illumination ("dark control").

FIG. 7 shows XPS spectra of TFAAD on zirconium oxide, bare zirconium oxide, and a sample exposed to TFAAD but no UV illumination ("dark control"). Only the functionalized surface shows a fluorine peak. In addition, the carbon peak is largest for the functionalized surface.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

All publications, patent applications, issued patents, and other documents referred to in this specification are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

What is claimed is:

1. A functionalized metal oxide comprising:
   a metal oxide; and
   at least one linker molecule covalently bound to the metal oxide via an anchoring group,
   wherein the at least one linker molecule comprises the anchoring group, the anchoring group is a carbon, a CH group, or a $CH_2$ group, and the anchoring group is covalently bound directly to the metal oxide without any intervening atoms between the carbon of the anchoring group and the metal oxide,
   and further wherein, the at least one linker molecule comprises a functional group and a dye molecule is covalently bound to the linker molecule via the functional group.

2. The functionalized metal oxide of claim 1, wherein the functional group is selected from a protected or unprotected carboxylic acid group or a protected or unprotected amine group.

3. The functionalized metal oxide of claim 1, wherein the at least one linker molecule is the reaction product of a linker precursor and the metal oxide, further wherein the linker precursor comprises a substituted or unsubstituted alkene or a substituted or unsubstituted alkyne, and further wherein the at least one linker molecule comprises a substituted or unsubstituted alkane, a substituted or unsubstituted alkane, a substituted or unsubstituted alkene, or a substituted or unsubstituted alkyne.

4. The functionalized metal oxide of claim 1, wherein the metal oxide comprises doped or undoped $TiO_2$, ZnO, $ZrO_2$, or $SnO_2$.

5. The functionalized metal oxide of claim 1, wherein the metal oxide comprises a nanocrystalline, porous structure.

6. The functionalized metal oxide of claim 1, wherein the metal oxide comprises a non-porous structure.

7. The functionalized metal oxide of claim 1, wherein the metal oxide is disposed over the surface of a substrate.

8. The functionalized metal oxide of claim 7, wherein the substrate is selected from glass or plastic.

9. A dye-sensitized solar cell comprising the functionalized metal oxide of claim 1.

10. The functionalized metal oxide of claim 1, wherein the at least one linker molecule is the reaction product of a linker precursor and the metal oxide, further wherein the linker precursor is a substituted or unsubstituted alkyne, and further wherein the at least one linker molecule is a substituted or unsubstituted alkene or a substituted or unsubstituted alkyne.

11. The functionalized metal oxide of claim 1, wherein the metal oxide is patterned with an array, the array comprising one or more areas having the at least one linker molecule and one or more areas without the at least one linker molecule.

12. The functionalized metal oxide of claim 11, wherein the at least one linker molecule in one area of the array is different from another linker molecule in another area in the array.

* * * * *

UNITED STATES PATENT AND TRADEMARK OFFICE
CERTIFICATE OF CORRECTION

| | |
|---|---|
| PATENT NO. | : 8,093,177 B2 |
| APPLICATION NO. | : 12/266130 |
| DATED | : January 10, 2012 |
| INVENTOR(S) | : Robert J. Hamers et al. |

It is certified that error appears in the above-identified patent and that said Letters Patent is hereby corrected as shown below:

IN THE CLAIMS:

Col. 14, line 57 (Claim 3)

Delete "a substituted or unsubstituted alkane,"

Signed and Sealed this
Nineteenth Day of June, 2012

David J. Kappos
*Director of the United States Patent and Trademark Office*